(12) United States Patent
Pitchaimani

(10) Patent No.: US 11,601,412 B2
(45) Date of Patent: *Mar. 7, 2023

(54) SECURELY MANAGING DIGITAL ASSISTANTS THAT ACCESS THIRD-PARTY APPLICATIONS

(71) Applicant: VMware, Inc., Palo Alto, CA (US)

(72) Inventor: Saravanan Pitchaimani, Atlanta, GA (US)

(73) Assignee: VMware, Inc., Palo Alto, CA (US)

( * ) Notice: Subject to any disclaimer, the term of this patent is extended or adjusted under 35 U.S.C. 154(b) by 307 days.

This patent is subject to a terminal disclaimer.

(21) Appl. No.: 16/944,579

(22) Filed: Jul. 31, 2020

(65) Prior Publication Data

US 2020/0360119 A1 Nov. 19, 2020
US 2022/0338964 A9 Oct. 27, 2022

Related U.S. Application Data

(63) Continuation of application No. 15/796,959, filed on Oct. 30, 2017, now Pat. No. 10,749,855.

(51) Int. Cl.
*H04L 9/40* (2022.01)
*G06F 21/44* (2013.01)
*G06F 21/41* (2013.01)

(52) U.S. Cl.
CPC .......... *H04L 63/0815* (2013.01); *G06F 21/41* (2013.01); *G06F 21/44* (2013.01);
(Continued)

(58) Field of Classification Search
CPC ............... H04L 63/0815; H04L 63/083; H04L 63/0884; G06F 21/41; G06F 21/44; G06F 2221/2111; G06F 2221/2137
See application file for complete search history.

(56) References Cited

U.S. PATENT DOCUMENTS 10,255,922 B1 4/2019 Sharifi
10,304,463 B2 5/2019 Mixter
(Continued)

OTHER PUBLICATIONS

Alotaibi, Aziz, "'Enhancing OAuth Services Security by an Authentication Service with Face Recognition'", IEEE, NY, USA, 2015, 6 Pages.
(Continued)

*Primary Examiner* — Catherine Thiaw
(74) *Attorney, Agent, or Firm* — Clayton, McKay & Bailey, PC

(57) ABSTRACT

Systems herein allow a digital assistant to make requests to applications, such as third-party applications, that access data in an enterprise mobility management ("EMM") system. The digital assistant can link to a portal application and receive a token that identifies a user. A remote application on a user device can establish a session with the portal application as part of a single sign on ("SSO"). The session can identify the same user. The portal application can then link the digital assistant to the remote application. When the digital assistant makes a request to the portal application, a notification can be pushed to the remote application. The user can confirm the request, establishing an authorized session during which time the digital assistant can make additional requests to the portal application. The portal application can service the requests by accessing third-party applications available through the portal application and authorized for access by the SSO.

20 Claims, 9 Drawing Sheets

(52) U.S. Cl.
CPC ........ *H04L 63/083* (2013.01); *H04L 63/0884* (2013.01); *G06F 2221/2111* (2013.01); *G06F 2221/2137* (2013.01)

(56) References Cited

U.S. PATENT DOCUMENTS

| | | |
|---|---|---|
| 11,217,255 B2 * | 1/2022 | Kim .................. G10L 15/22 |
| 2007/0061460 A1 | 3/2007 | Khan |
| 2007/0185718 A1 | 8/2007 | Di Mambro |
| 2009/0286506 A1 | 11/2009 | Gu |
| 2013/0097682 A1 | 4/2013 | Zeljkovic |
| 2013/0298201 A1 | 11/2013 | Aravindakshan |
| 2013/0311191 A1 | 11/2013 | Deng |
| 2014/0032691 A1 | 1/2014 | Barton |
| 2014/0082715 A1 | 3/2014 | Grajek |
| 2014/0096219 A1 | 4/2014 | Lang |
| 2015/0200948 A1 | 7/2015 | Cairns |
| 2016/0149958 A1 | 5/2016 | Singh |
| 2016/0262017 A1 | 9/2016 | Lavee |
| 2016/0314299 A1 | 10/2016 | Almer |
| 2016/0314792 A1 * | 10/2016 | Alvarez Guevara ... G10L 15/08 |
| 2017/0324565 A1 | 11/2017 | Gattu |
| 2017/0359334 A1 | 12/2017 | Maddox |
| 2018/0000706 A1 | 1/2018 | Leblang |
| 2018/0101422 A1 | 4/2018 | Flanigan |
| 2019/0036923 A1 | 1/2019 | Xuan |

OTHER PUBLICATIONS

Bijani, Chaya , et al., "Giving Voice to Enterprise Mobile Applications", MobileHCI, Aug. 27-30, 2013, Munich, Germany, ACM, Aug. 27, 2013, 428-433.

* cited by examiner

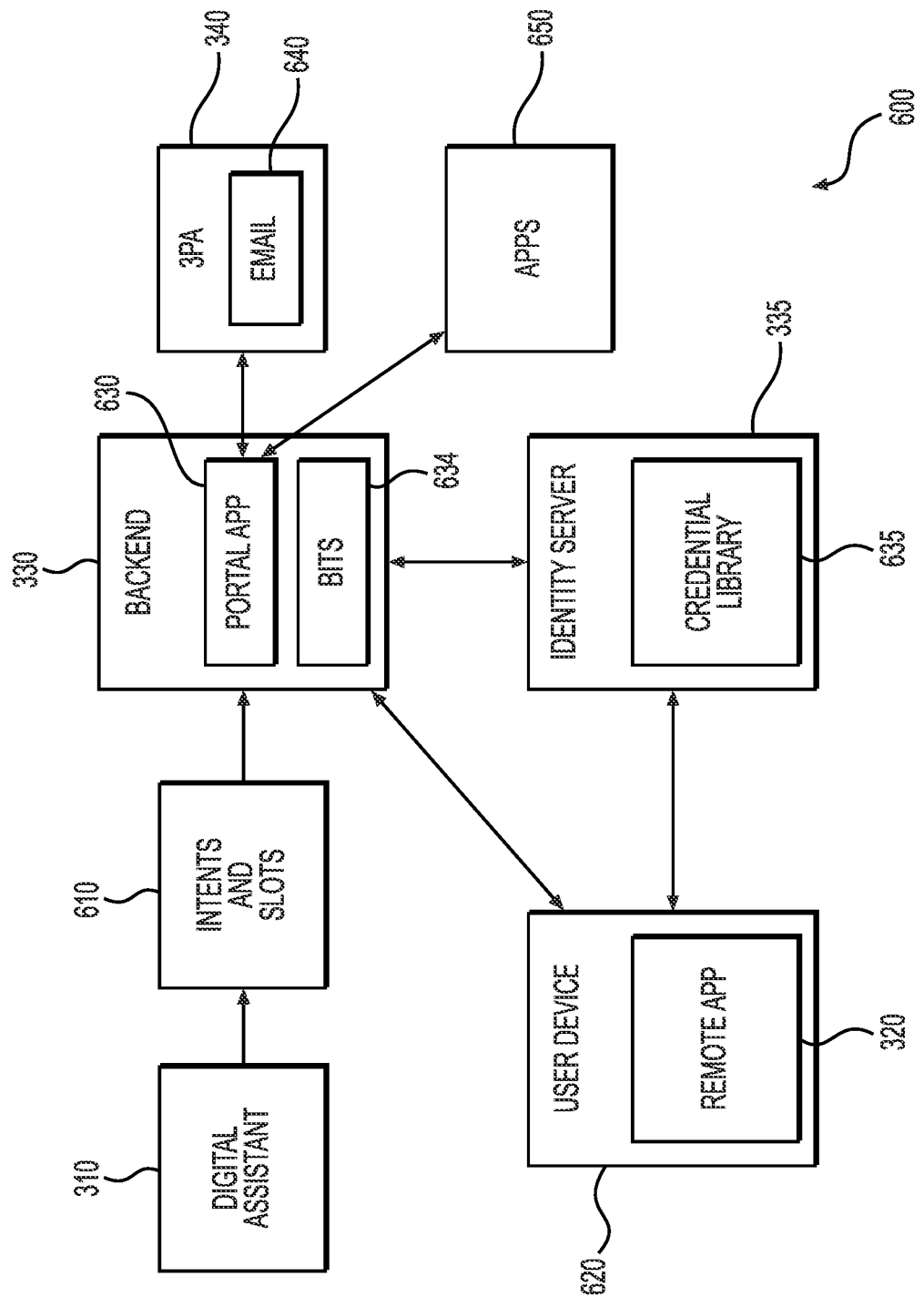

SECURELY MANAGING DIGITAL ASSISTANTS THAT ACCESS THIRD-PARTY APPLICATIONS

This application is a continuation of, and claims priority to, U.S. patent application Ser. No. 15/796,959 entitled, "SECURELY MANAGING DIGITAL ASSISTANTS THAT ACCESS THIRD PARTY APPLICATIONS," filed Oct. 30, 2017, which is hereby incorporated by reference in its entirety for all purposes.

BACKGROUND

Enterprise mobility management ("EMM") systems have gained tremendous popularity. They generally enable employees to use their own personal computing devices for work purposes, allowing enterprises to save money by purchasing fewer dedicated computing devices. Enterprises gain productivity by implementing an EMM system because employees can conveniently perform work tasks from their own devices. In addition, the management features of EMM systems can prevent sensitive data from leaving work applications, which are often managed by the EMM system.

The EMM system can grant the user access to third-party applications, such as email, by logging into the third-party application on behalf of the user. For example, the user can sign into the EMM system using single sign on ("SSO"). Then, when the user attempts to open their corporate email, the EMM system can log into the email application on behalf of the user. This can allow the EMM system to control a user's access to corporate email and other third-party applications.

Another growing technology is that of digital assistants, such as SIRI, ALEXA, GOOGLE Assistant, and CORTANA. Users can speak a request, such as a question or command, to the digital assistant. The associated audio is parsed and a relevant service attempts to fulfill the request. The detected audio request can be turned into an API call to a third-party server, and the digital assistant can provide user credentials to log in and retrieve a result. For example, a user can say "ALEXA, play me a song from the Rolling Stones" and the digital assistant can contact a service, supply user credentials, and retrieve an appropriate song.

However, digital assistants have not yet been successfully integrated with enterprise applications. This is because EMM systems have not yet had a way to manage the security of digital assistants. The EMM system often does not directly control either the digital assistant or the third-party service. Instead, the EMM system needs to act as an intermediary in order to retain control over the user's access to enterprise data. Integrating digital assistants while maintaining the EMM system as an intermediary has proven problematic. Normally, a digital assistant would store the access credentials for directly accessing a third-party application. But doing so would compromise the EMM system's control over enterprise data.

Likewise, the EMM system needs some way to verify that the person using the digital assistant is actually an enrolled user of the EMM system. For example, anyone near a digital assistant associated with the user could say, "SIRI, open my email and read it." If the digital assistant could directly access the email, it could read sensitive information to someone other than the user without appropriate control and oversight by the EMM system.

The security measures of an EMM system can also negate convenience advantages of a digital assistant. For example, if the user must log into an application each time the digital assistant tries to carry out a request, there would be little point in using a digital assistant. The main reason to do so is the convenience of just talking to the device. If each request required the user to log in, digital assistants would not be useful for accessing enterprise data in the third-party applications.

As a result, a need exists for managing access of third-party applications by digital assistants.

SUMMARY

An example system manages digital assistant access to third-party applications. A digital assistant can receive voice requests and fulfill them by making requests to a linked service. A user can link a service to the digital assistant through use of an interface, such as a web browser, that allows access to an account associated with a digital assistant. The account can allow the user to add services or skills to the digital assistant, expanding the types of requests that the digital assistant can attempt to fulfill.

In one example, the user can link the digital assistant to a portal application that is part of an enterprise mobility management ("EMM") system. The portal application can execute as a web application or an installed application on a user device, such as a phone or tablet. Using the portal application, such as WORKSPACE ONE, the user can access one or more third-party applications. The third-party applications can be email or other enterprise applications, such as OUTLOOK or SALESFORCE. The portal application can store a user's credentials and provide the user with access to any of the applications represented by the icons displayed on the user device by authenticating the user to the applications. For example, the portal application can use SSO to provide access to third-party applications. A user profile on a management server can specify which third-party applications are available to the user. These third-party applications and other enterprise applications can be called first and second applications herein, and can be accessed through the portal application.

The request to link the digital assistant to the portal application can be received by the backend server of the portal application. For example, linking the account of the digital assistant to the portal application can automatically direct the user to a webpage to the backend server. The backend server can then prompt the user to login. Using a user device, the user can be authenticated at an identity server that can be separate from or part of the backend server. The identity server can check the user's login credentials to make sure the user is enrolled in the EMM system.

After verifying the user, the identity server can return a token, such as an OAuth token, to the backend server. This linking token can identify the user associated with the digital assistant. The digital assistant can store and use this linking token when making requests to the portal application. This can allow the portal application to identify the user expected to be associated with the digital assistant.

However, to ensure that an individual using the digital assistant is an enrolled user, an additional layer of authentication can be provided. In one example, a remote application can execute on a user device associated with the user. The remote application can allow the user to authorize sessions or requests from the linked digital assistant. The remote application can be installed on the user device or can be a web application accessed by the user device.

In one example, the remote application authenticates with the identity server separately from the digital assistant. The remote application can authenticate the user when the user logs into the portal application or the EMM system. The remote application can use Security Assertion Markup Language ("SAML") or OAuth to authenticate itself with an identity server as part of SSO in one example. When the user's identity is verified, the remote application can connect to the backend server. In one example, the remote application can make an assertion, such as a SAML assertion at the backend server. The SAML assertion can contain identifying information that allows the backend server to identify the user. Other assertions, such as tokens, are also possible. This can establish a session between the remote application and the backend server.

Using both the assertion and the linking token, the backend server can determine that the same user is associated with both the digital assistant and the remote application. This can allow the backend server to link the digital assistant to the remote application. Using this link, the backend server can ensure that the user at the remote application approves of the digital assistant's requests.

When a user makes a request at the digital assistant that requires access to a third-party application available at the portal application, the backend server can determine whether the user has authorized the digital assistant to send requests through the portal application. If the authorized session is not yet active, the backend server can push a notification to the remote application. The remote application can display a prompt for the user to validate the request of the digital assistant. For example, the prompt can state, "Do you approve the request made by your ALEXA?" The user can approve the request using the remote application. This can create an authenticated session token that is valid for a period, such as ten minutes. The session token can be stored at the backend server. While the session token is valid, the backend server can use the session token to access third-party applications on behalf of the digital assistant. The digital assistant can make repeated requests within the time allotment without further manual verification from the remote application, in an example.

This process can allow an EMM system to provide the digital assistant with managed access to the third-party applications. In one example, the user does not need to individually log into the third-party applications. Instead, the identity server can maintain a library of OAuth tokens and other credentials for logging the user into multiple different third-party applications. The authorized session can allow the portal application to provide access on behalf of the digital assistant based on the other OAuth tokens stored by the identity server.

Access can be limited to particular third-party applications in one example. Users can have access to different applications based on profiles stored at the management server. In one example, the user can indicate which third-party applications the digital assistant can access. This can allow a user to enable some of their enterprise applications for use with the digital assistant, but not others. In one example, the session token stored at the backend server can indicate which third-party applications are available to the digital assistant. In one example, the identity server can use these settings to determine which OAuth tokens to send to the backend server for accessing the applications.

The management server, backend server, or remote application can also revoke access to one or more of the third-party applications. For example, an administrator can revoke user access to some or all applications, such as when the user leaves the company. Additionally, the user can select which applications the digital assistant is allowed to access in an example. The selection can be a subset of the full suite of applications available to the user through the portal application.

It is to be understood that both the foregoing general description and the following detailed description are exemplary and explanatory only and are not restrictive of the examples, as claimed.

BRIEF DESCRIPTION OF THE DRAWINGS

FIG. 6 is an exemplary illustration of system components.

DESCRIPTION OF THE EXAMPLES

Figure 1:
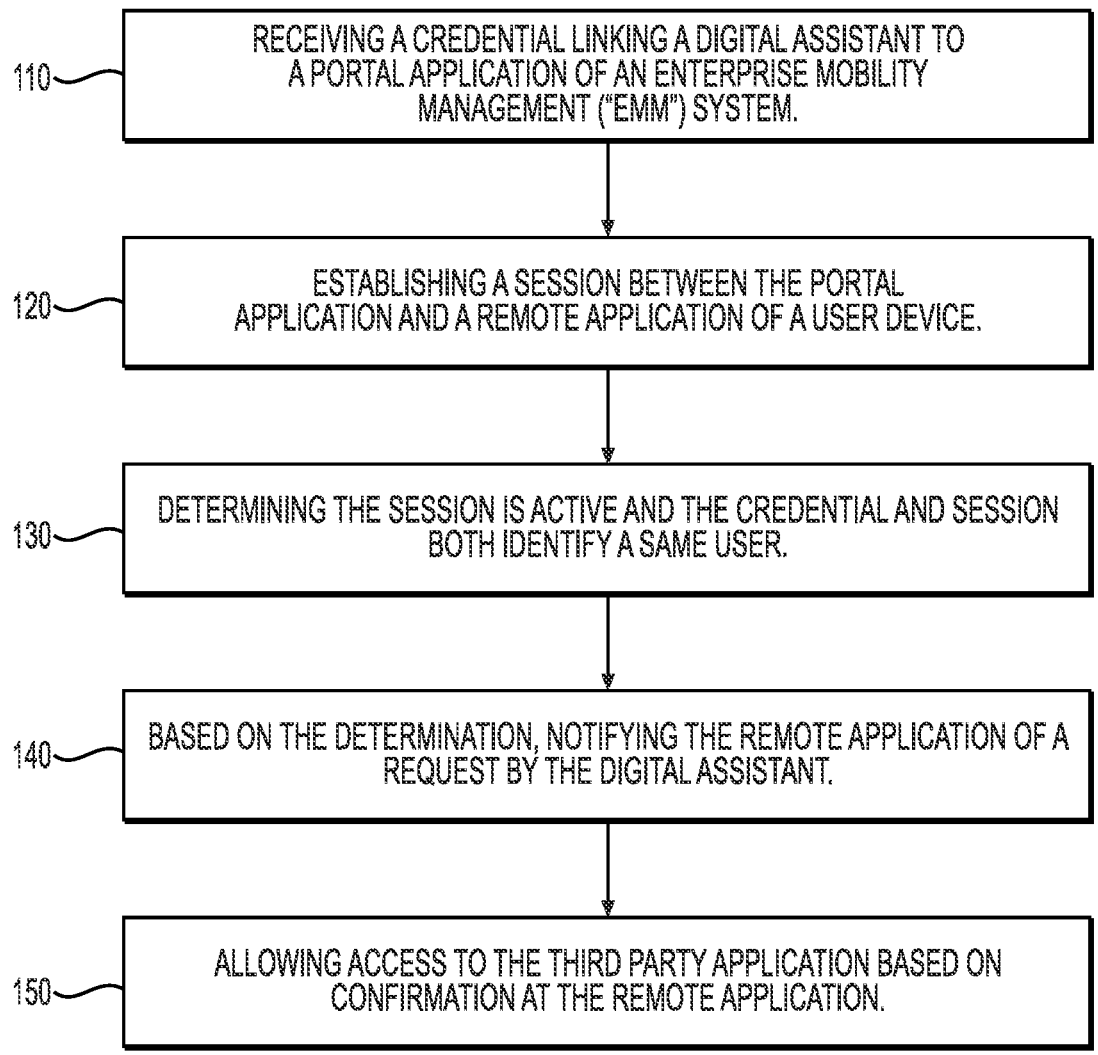
FIG. 1 is an exemplary flow chart of steps performed in a system.

Reference will now be made in detail to the present examples, including examples illustrated in the accompanying drawings. Wherever possible, the same reference numbers will be used throughout the drawings to refer to the same or like parts.

An example system can allow a user's digital assistant to utilize third-party applications that access enterprise data in an EMM system. In one example, both the digital assistant and third-party application can be maintained separately from the EMM system, while still allowing the EMM system to control transactions and maintain enterprise security.

A digital assistant can be any device that receives audio commands to access a service and return a result. Examples include SIRI, ALEXA, GOOGLE Assistant, and CORTANA. Alternatively, the digital assistant can persist on a user device, such as a phone or tablet.

To access the third-party application, such as OUTLOOK, the digital assistant can first link with a portal application. The portal application can serve as an access point for applications authorized for use in the EMM system. The portal application can present different applications (including third-party applications) for the user, depending on the user's profile within the EMM system. The portal application can be a web application or can be installed on a user device. The portal application can require enrollment in the EMM system before the user can access some or all of the applications available through the portal application.

In one example, the user can link their digital assistant to the portal application. The user can go to an account screen, such as by using a browser on their user device, and direct the digital assistant to link with the portal application. The digital assistant or user device can connect with the portal application by contacting a backend server with a link request. The portal application can then prompt the user to login. Upon verifying the login, the backend server can return a token, such as an OAuth token, for use by the digital assistant in future communications with the portal application. The OAuth token can include an encrypted user identifier in an example. The user identifier can be a number, code, email address, or name of a user. This can allow the digital assistant to identify itself as associated with the user.

As a second layer of authentication, the user can also log into the EMM system using a user device. The login can be part of an SSO process and require the user to be enrolled in the EMM system. An identity server can authenticate the user and cause the user device to connect to the backend server of the portal application.

In one example, the user device authenticates and connects to the backend server by executing a remote application. The remote application can establish a session with the portal application. To do this, the remote application can assert a user identifier, such as in a token or in a SAML assertion. The portal application can identify the same user from both the assertion and the OAuth token. This allows the backend server of the portal application to associate the digital assistant with the remote application at the user device.

When the digital assistant requests the portal application for access to a third-party application, the portal application can determine whether an active session exists. If not, the remote application can prompt the user at the user device to approve the request. Approval activates a timed session at the backend server. While the session is active, the digital assistant can access some or all of the third-party applications that the user can access as part of their SSO with the EMM system.

FIG. 1 includes exemplary stages performed by a backend server that executes a portal application in an EMM system. At stage 110, the digital assistant links with the portal application. To do this, a user can navigate a graphical user interface ("GUI") associated with the digital assistant, such as a web interface. The web interface can be retrieved on a user device that is separate from the digital assistant in one example. Alternatively, the digital assistant can retrieve it. The GUI can include an option to link the digital assistant to one or more applications or services. One such application or service can be the portal application.

The portal application can be an application that provides varying levels of access to multiple other applications. These applications may or may not be installed on the user device. Users enrolled in the EMM system can use the portal application, such as WORKSPACE ONE, to access third-party applications deployed as part of the EMM system. The portal application can give the user access to enterprise-related applications, including third-party applications such as OUTLOOK and SALESFORCE. In one example, the portal application is a web application that a user device can access over a network, such as the Internet. Alternatively, a portal application can be installed on the user device.

When accessed by a user device, the portal application can display application icons for any icons the user can access, or could potentially access, such as third-party applications. To access the applications, the user device can first authenticate with the portal application. This can be an SSO authentication. The portal application can then authenticate on the user's behalf at the other applications. The portal application or a separate identity server can store credentials for logging the user into the various other applications accessible through the portal application.

For the digital assistant to access a third-party application that is available through the portal application, a two-part authentication process can take place. At stage 110, when the user selects an option to link the digital assistant to the portal application, the GUI or digital assistant can contact the backend server. If the digital assistant has not yet linked to the portal application, then it will not yet possess a token to identify itself. As a result, the portal application can prompt the user to login.

The login can be verified by the backend server or a separate identity server. When a user recognized by the EMM system logs in, the backend server can send an OAuth token to the digital assistant. The OAuth token can include an encrypted user identifier. The backend server can decrypt the OAuth token and determine the user's identity.

However, a second authentication factor can be used to help ensure that the digital assistant is actually being used by the enrolled user, rather than by an unauthorized or unknown user. In one example, the user device can sign into the EMM system with SSO. The SSO can use SAML. In one example, a remote application can contact the backend server or identity server to log into the EMM system. The remote application can be a web application or an installed application. The remote application can also be part of an agent application that allows an EMM system to manage some functionality of the user device. In one example, the remote application requests an SSO service from the identity server. After validating the user device or user, the identity provider can respond with an XHTML form, in one example. This can give the user device an address or other credential needed to make a SAML assertion to the backend server.

At stage 120, the remote application of the user device can establish a session with the portal application. For example, the identity server can make the SAML assertion to the backend server. This can authenticate the remote application with the backend server and establish the session. The session can allow the remote application and backend server to send messages to one another over a network.

The SAML assertion can also identify the user. At stage 130, the backend server can determine that the session is active and identifies the same user as the OAuth token presented from the digital assistant. This can allow the backend server to associate the remote application at the user device with the digital assistant.

At stage 140, the backend server can send a notification to the remote application, indicating the portal application has received a request from the digital assistant. For example, the digital assistant can request access to a third-party application that is available through the portal application. As an example, a user can say, "SIRI, open the portal app and read my email." The digital assistant can make a request to the portal application to open and return unread or recent emails. If the request is authorized, the portal application can open the third-party email application using credentials from the SSO. The request from the digital assistant can be an API call to the portal application in one example. The API call can cause the portal application to open the third-party email application, such as OUTLOOK, if the portal application determines the digital assistant is permitted to do so.

The backend server can check whether a session is active with the remote application. If not, it can send a message back to the digital assistant that can cause the digital assistant to tell the user to log into the EMM system. For example, the digital assistant can say "Please log into the EMM system with your user device so I can send you a request."

If the session is active between the backend server and remote application, the backend server can send the notification to the remote application at stage 140. The notification can appear on the screen of the user device. In one example, the notification can be a message displayed by the remote application or the operating system ("OS") of the computing device. For example, the notification can state, "There has been a request made by your SIRI. How would you like to proceed?" The remote application can present an option to authorize the request or deny the request. The notification can also go to the digital assistant, in one example. This can allow the digital assistant to inform the user that they need to authorize the digital assistant on their user device.

When the user chooses to confirm authorization, an authorization period can begin. During that period, the digital assistant can access one or more applications available through the portal application, including the third-party application. For example, some or all of the applications available to the user based on SSO at the portal application can be made available to the linked digital assistant, as will be described later in more detail.

Based on the confirmation at the remote application, at stage 150 the digital assistant can then access the third-party application. In one example, the backend server accesses the third-party application on behalf of the user. The backend server (or an identity server) can supply the credentials needed to access the third-party application. The backend server can receive the credential from the identity server in an example. The identity server can log the user into applications associated with the user's EMM profile as a background process. Upon doing so, the identity server can store the relevant tokens for accessing the applications. The backend server can use these tokens to access the third-party application.

The third-party application can perform an action based on an API call. The backend server can make the API call, in an example. In general, the API call can be based on the user's speech request (including questions and commands) to the digital assistant. The speech can be broken down into a single intent and optionally one or more slots by the digital assistant or a server that is dedicated to operating digital assistants. An intent indicates which service is responsible for handling the user's request. In this example, the service could be either the portal application or the third-party application. In either example, the intent can route the request to the portal application (i.e., backend server).

The slots can be variables that inform what the service needs to provide. For example, requesting unread email could yield different slots than requesting the five most recent emails. These variables can result in different searches, actions, or results from the portal application or third-party application.

In one example, using the intent and slots, the backend server can cause OUTLOOK can retrieve unread emails. The backend server can then forward some portion of those emails to the digital assistant for reading to the user. The backend server can also forward some portion of those emails for display at the remote application, in an example.

Figure 2:
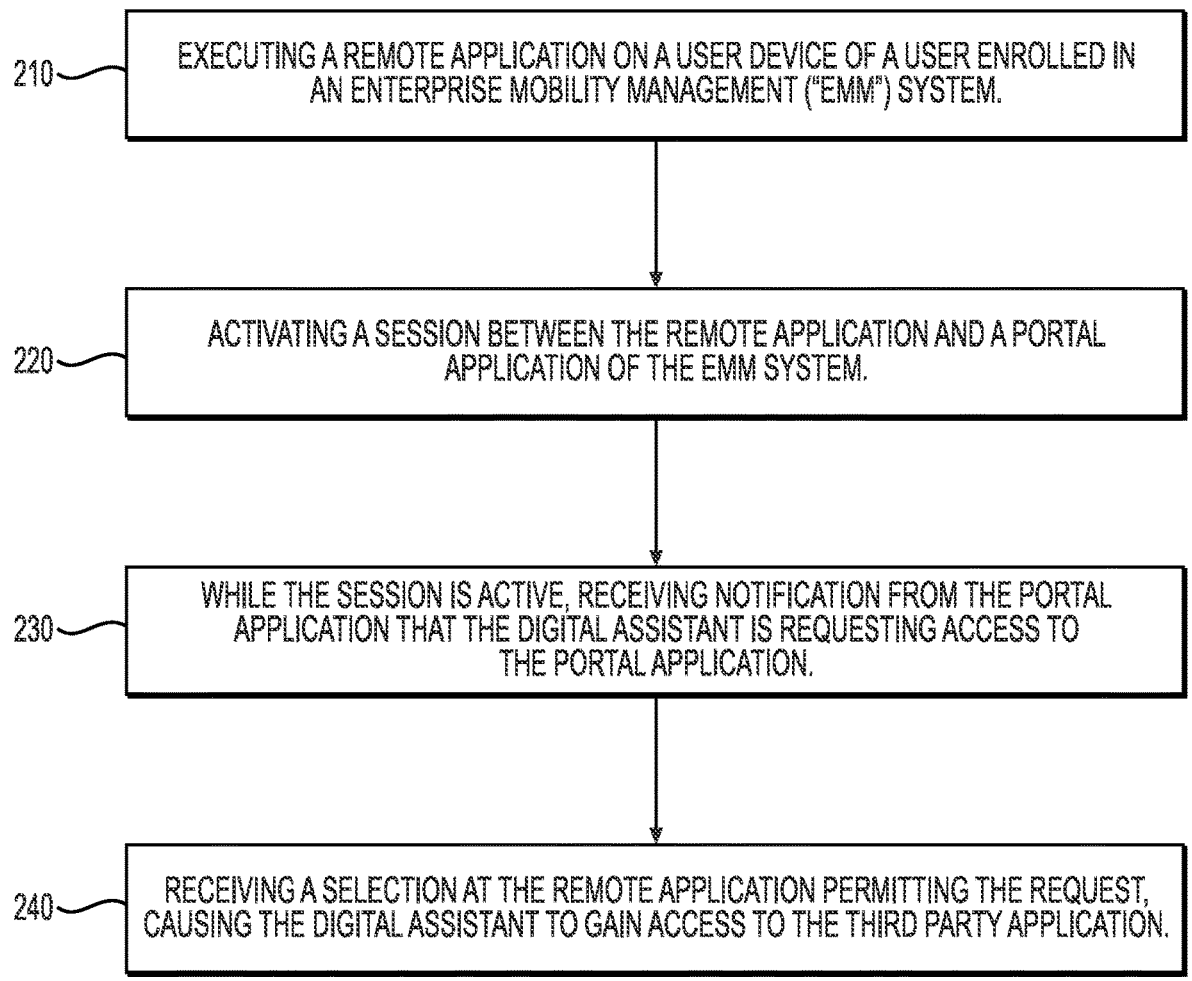
FIG. 2 is an exemplary flow chart of steps performed in a system.

FIG. 2 includes example stages performed by a remote application in an example. The remote application can be installed at the user device as part of enrollment in the EMM system in an example. Enrollment can allow the EMM system, such as the backend server or other management server, to collect information from the user device. It can also allow the EMM system to install managed applications on the user device, such as the remote application. The remote application can be part of a management agent in one example. If the OS on the user device does not already have the needed EMM functionality built in, then a management agent can allow the EMM system the requisite level of control over enterprise data and enterprise applications on the user device.

Alternatively, the remote application can be a web application. For example, a frontend of the portal application can execute in a web browser as the remote application at the user device.

At stage 210, the user device executes the remote application. This can occur when then user device logs into the EMM system, opens the remote application, or contacts the backend server through a web interface.

At stage 220, the remote application can begin a session with the portal application. This can occur when the remote application executes, which can require the user to sign into the EMM system. In one example, the remote application performs SSO at an identity provider, such as the identity server. The remote application can use SAML, OAuth, or another authentication method to authenticate itself with the identity server and connect to the backend server. In one example, the identity server verifies the user's identity and returns an XHTML form that directs the remote application to connect to the backend server. In one example, the remote application can make a SAML assertion that reveals the identity of the user to the backend server.

Once connected to the backend server based on the credentials from the identity server, the session begins and becomes active. The backend server can maintain the session with the remote application. The backend server can link the digital assistant and the remote application. This is because the SAML assertion from the remote application and the OAuth (or other) token from the digital assistant can both identify the same user. This link can allow for additional authentication of digital assistant requests at the remote application.

At stage 230, the remote application can receive a notification from the portal application of a request by the digital assistant. The purpose of this notification can be to get the user to confirm or verify that the digital assistant is authorized to access the applications provided by the portal application. There are several reasons why this additional layer of authentication is advantageous. As one example, the user might not actually be the one speaking their digital assistant. Instead, it could be someone else in the room attempting to do so.

When backend server receives the request from the digital assistant, the backend server can retrieve the user's identity from the OAuth token. For example, parameters in the OAuth token can be unique to the user, such as a tenant uniform resource locator in addition to an email address. The OAuth token can be a JSON web token ("JWT") encoded string based on user parameters. So when someone requests something from the digital assistant, the request can reach the backend with the JWT token. The backend server can then decrypt the JWT token to reveal the identity of the user who is believed to be making the request.

The backend server can then check that this user has an active session between their remote application and the backend. If so, the backend then pushes the notification to the remote application. If not, the backend server can return a message to the digital assistant that causes the digital assistant to prompt the user to execute the remote application or log into the EMM system with their user device.

The notification of stage 230 can cause the remote application or OS of the user device to display a message to the user. The message can notify the user that a digital assistant has made a request at the portal application.

At stage 240, the user can then confirm or deny the authorization of the digital assistant's request. If the user confirms authorization, the backend server can establish an authorization period or session in which the digital assistant can continue to make requests without further manual authorization at the remote application.

Additionally, the request can cause the portal application to access a third-party application. The available third-party applications can vary between users. User profiles can dictate which third-party applications are available for which users. For example, a programmer can be assigned different applications than a sales executive.

When the user signs into the portal application, a background service can log the user into a plurality of applications that access enterprise data. The tokens or other credentials for these applications can be stored at the backend server or identity server. The portal application can access and use these credentials to fulfill the request of the digital assistant. For example, a request to "open the portal application and read email" can cause the portal application to log into a third-party email application, such as OUTLOOK, using stored credentials. Then the portal application can retrieve and return an email from OUTLOOK to the digital assistant. In one example, this can allow an enterprise to authorize and control communications between a third-party digital assistant and a third-party application. Even without ownership over the software of either side, the EMM system can maintain control of its enterprise data.

In one example, the user can further select which applications available through the portal application are available to the user's digital assistant. For example, a GUI of the remote application or some other application can display the various applications available to the user as part of SSO at the portal application. The user can then select which of those applications to make available to their digital assistant. The selected applications can be represented in a profile or an array of bits that is stored at the backend server. For example, each potentially available application can be represented in the array of bits, with a "1" indicating an application can be accessed and a "0" indicating it cannot be accessed by the digital assistant.

Therefore, in one example, the backend server further determines whether the user has specified that the third-party application is accessible. If so, the backend server can carry out the request for the digital assistant. Otherwise, the backend server can return a message to the digital assistant, causing the digital assistant to notify the user to enable access to the third-party application.

Figure 3:
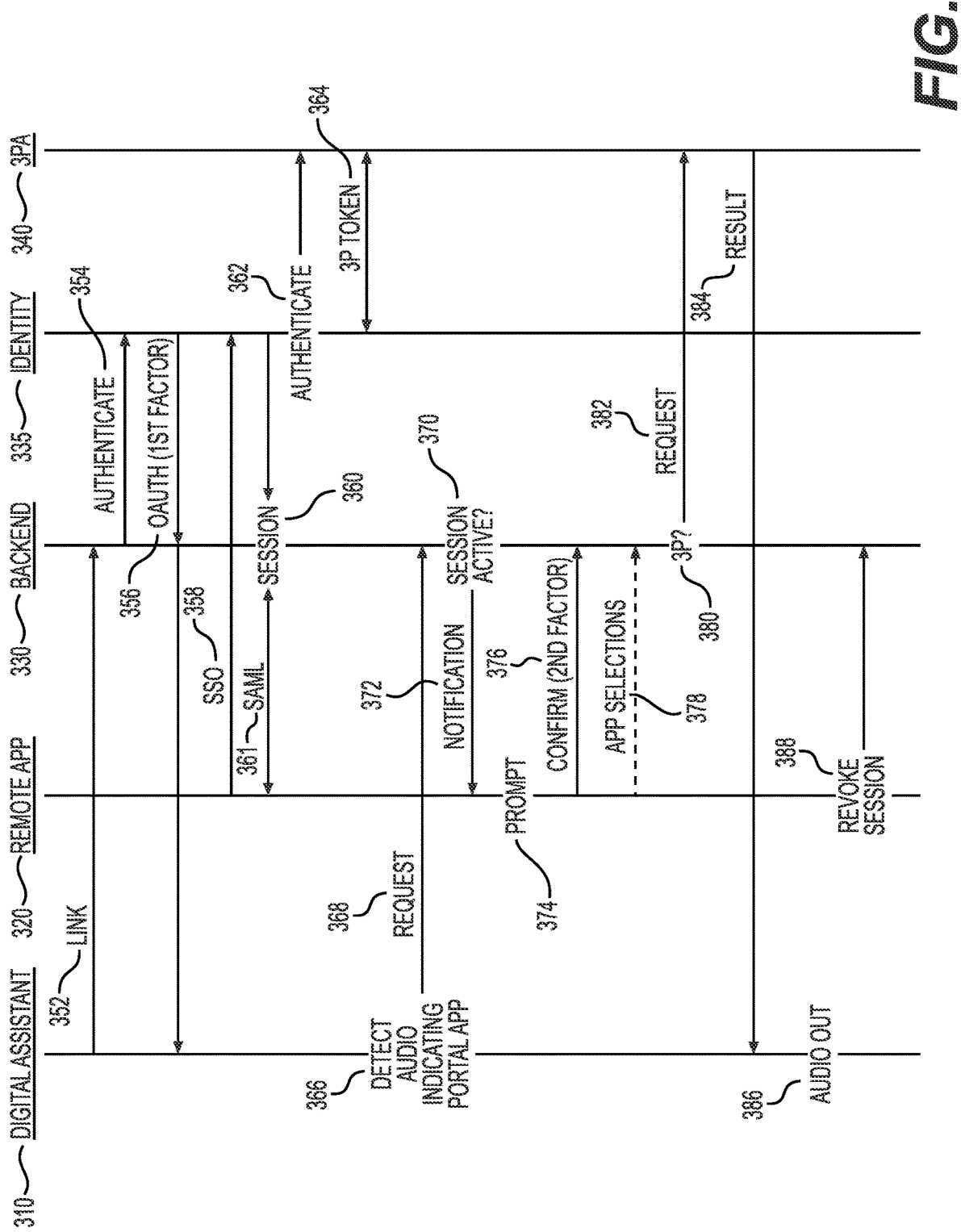
FIG. 3 is an exemplary flow chart of steps performed in a system.

FIG. 3 is another example method showing example stages performed by a digital assistant 310, remote application 320, backend server 330, identity server 335, and third-party application 340. At stage 352, the user can link the digital assistant 310 to the backend server 330 associated with the portal application. This can include logging into a digital assistant account to specify the link. In one example, the account is accessed in a web browser on a separate user device. The account can include an option to link various services. The linked services can define which intents the digital assistant 310 can respond to and which services will carry out the requests. In one example, the portal application is a service that the user can link to their digital assistant 310 in the account settings.

When the link is attempted at stage 352, the backend 330 can prompt the user to authenticate themselves with the portal application at stage 354. If the user has not already identified themselves in relation to the digital assistant 310, the user can be prompted to authenticate at the identity server 335. If the user enters a valid user ID, password, or other credential, the identity server 335 can return an OAuth token at stage 356. The token can be stored at the backend 330 and supplied to the digital assistant 310 for future interactions with the backend. The OAuth token can identify the user. It can be encrypted or the user identifier(s) can be encrypted. In either example, the backend can extract information from the OAuth token that is used to identify the user.

At stage 358, a remote application 320 can perform SSO with the identity server 335. This can happen, for example, when the user device logs into an EMM system or attempts to access the portal application. The identity server 335 can return information that causes the remote application 320 to contact the backend server 330.

At stage 360, this results in the remote application 320 establishing an active session at the backend server. The remote application 320 can make an SAML assertion at stage 361 when it contacts the backend server 330. The SAML assertion can identify the user. The backend server 330 can then associate the instance of the remote application 320 with the digital assistant 310 based on both the digital assistant 310 and remote application 320 identifying the same user to the backend server 330. This link between the remote application and the digital assistant can allow for another layer of authentication.

Meanwhile or afterwards, at stage 362 the identity server 335 or another service can authenticate the user at multiple applications accessible through the portal application as part of the user's SSO. In one example, the backend server 330 or some other management server maintains user profiles that specify which applications and repositories the user can access within the EMM system. The identity server 335 or backend server 330 can retrieve and store credentials on the user's behalf for accessing these permitted applications and repositories.

In one example, the available applications and repositories can be based on a group to which the user belongs within the enterprise. For example, programmers might have access to a different suite of applications than sales employees. The user's group can be indicated by the user profile in an example.

As part of the authentication at stage 362, the service can authenticate the user with the third-party application 340. In response, the identity server 335 can send tokens or other credentials to the backend server 330 at stage 364. The credentitals can be used to access the third-party application 340, in an example. This can prevent the need for the digital assistant 310 or user device to reenter credentials once fully credentialed at the portal application.

With the digital assistant 310 linked to the remote application 320 at the backend server 330, the system is setup to allow the user to confirm or deny the digital assistant's 310 requests to use the portal application.

At stage 366, the user can speak to the digital assistant and make a request. For example, the request could be "open the portal application and read my new email." At stage 368, a service running at the digital assistant 310 or at a server can parse the audio. The audio is parsed into an intent and at least one slot. The intent can indicate which service to contact, whereas the slots can indicate which functions or variables to provide to the service. In this example, the intent indicates the portal application should be contacted. As a result, at stage 368, the digital assistant sends a request to the backend server 330.

The request of stage 368 can include intent(s) and slot(s), and can be sent with the OAuth token received at stage 356.

This allows the backend server 330 to determine the user that should be associated with the request from the digital assistant 310.

At stage 370, the backend server 330 determines whether that user also has an active session between their remote application 320 and the backend server 330. If not, the backend server 330 returns a message to the digital assistant, causing it to tell the user to sign into the EMM system or execute the remote application.

Conversely, if the session is active, the backend server 330 pushes a notification to the remote application 320 at stage 372. The notification can cause the remote application 320 to prompt the user at stage 374. The prompt can notify the user that the digital assistant has sent a request to the portal application. The prompt can further ask the user to confirm whether to allow the request.

At stage 376, the user can confirm the digital assistant 310 is authorized to make the request. If confirmed, an authorization session can begin at the backend server 330, allowing the digital assistant 310 to continue making requests without requiring further confirmation for a period. For example, the authorization session can be set to last for 10 minutes.

At stage 378, a user or administrator can select which applications the digital assistant 310 can or cannot access. For example, even though the user's profile can specify ten different applications are available to the user through the portal application, the user can specify which of those should be accessible to the digital assistant 310. Likewise, if the enterprise deems some applications too sensitive for audio delivery by a digital assistant 310, the user profile can restrict the digital assistant from accessing them. For example, applications that access invoicing, tax information, HR information, or for viewing legally protected information can be flagged as inaccessible in a user profile. In some cases, accessibility by digital assistants can be defined based on user groups. For example, an executive user group might be allowed to use their digital assistants with sensitive data or applications whereas a sales user group can be restricted from similar usage.

To allow the backend server 330 to discern which applications are available to the digital assistant 310, the backend server 330 can store an array of bits associated with the user. Each bit can be a zero or one and represent whether or not an application is accessible to the digital assistant 310. As an example, if ten applications are available to the user in the portal application, the array of bits can be ten digits long. Each digit can represent one of the applications. If second digit is a one, this indicates that the second application is available for requests from the digital assistant 310. If the second digit is a zero, the second application is unavailable to the digital assistant 310.

Therefore, at stage 380, the backend server 330 can further check whether the third-party application 340 is available to the digital assistant 310. If it is, then at stage 382 the backend server 330 can forward the request to the third-party application 340. The request can be accompanied with a token stored as part of stage 364. The request can also be formatted as an API call to the third-party application 340. The API call can be formatted based on the intent and slots determined at stages 366 and 368.

At stage 384, the third-party application 340 can return a result to the backend server 330 or digital assistant 310. At stage 386, the digital assistant reads the result to the user. This can include reading the text of an email or explaining what it has retrieved In one example, the remote application 320 allows the user to revoke the authorization session at stage 388. For example, even though the digital assistant's authorized session might have several more minutes remaining, the user can cut the session short. This can be useful, for example, if the user is leaving the digital assistant 310. By revoking the session, the digital assistant 310 will be blocked from accessing the portal application or the third-party application 340 until another authorized session is established.

In one example, the remote application 320 includes a GUI option to revoke the session. The user can simply revoke the session by selecting the option. In another example, the session is revoked when the user device (executing the remote application) moves outside of a geofenced area. The user can set up a geofence around the digital assistant 310 in one example. This can allow the remote application 320 to automatically revoke the session based on the user device leaving a geofenced area of the digital assistant 310. Revoking the session can cause the backend server 330 to delete the bits indicating which applications can be accessed, in an example.

Figure 4:
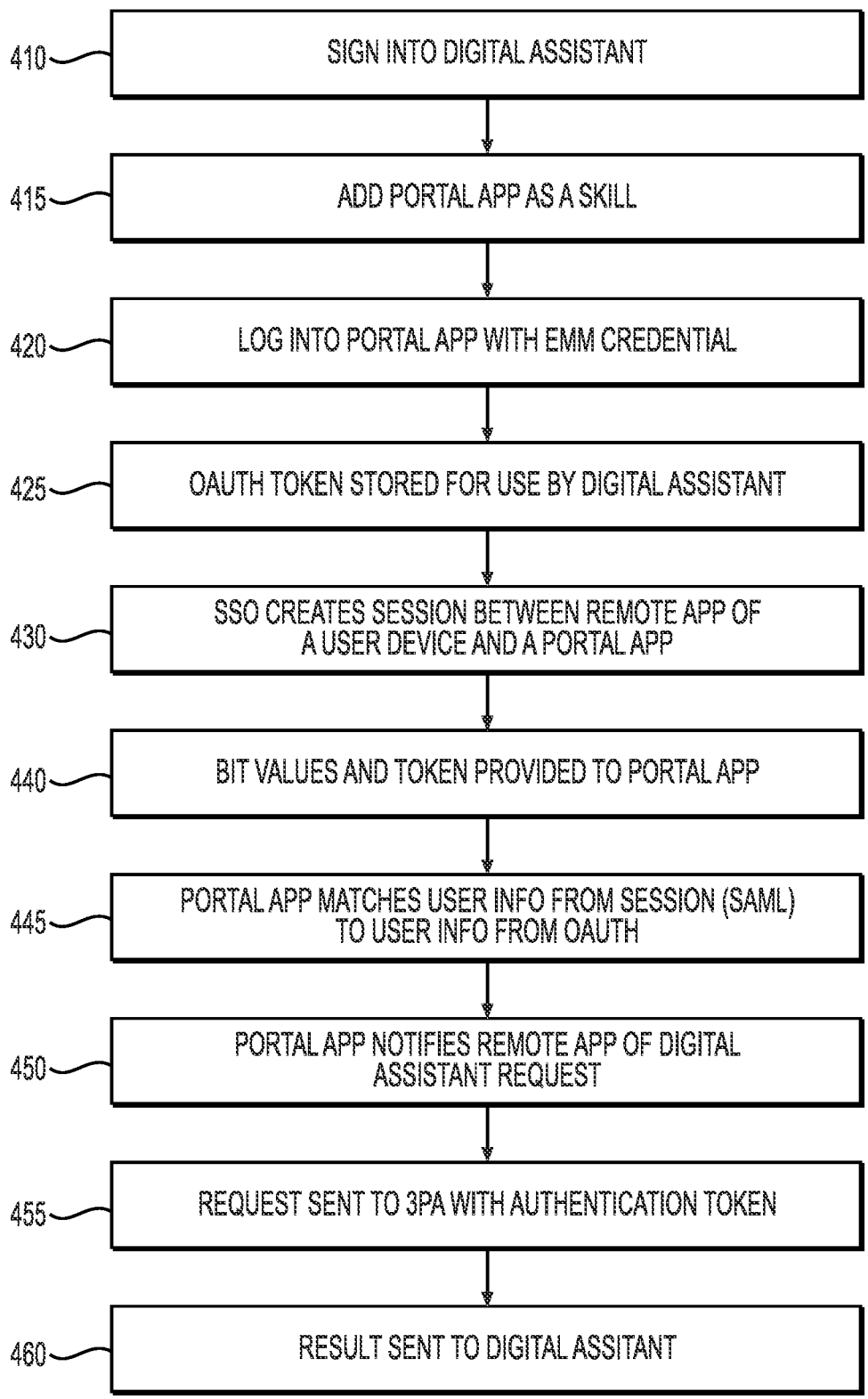
FIG. 4 is an exemplary flow chart of steps performed in a system.

FIG. 4 is another example flowchart that shows stages performed by the digital assistant 310, remote application 320 of the user device, and portal application. At stage 410, the user can sign into an account for the digital assistant 310. For example, the user can open an application or website to access the account. From within the account, the user can link the digital assistant 310 to various backend services, including the portal application. In one example, the linking can be referred to as adding a skill to the digital assistant 310. At stage 415, the user can add the portal application as a skill to the digital assistant 310.

At stage 420, to complete the linking, the user can be prompted to log into the portal application. The user can supply their password or a token recognized by the EMM system. This can allow an identity service, such as the identity server 335, to verify and authenticate the user. At stage 425, the identity service can return an OAuth token to the backend server 330 of the portal application. The backend server 330 can store the OAuth token and provide a copy to the digital assistant for use in future communications with the portal application. In one example, the backend server 330 supplies the OAuth token to a digital assistant server that contacted the portal application to establish the linking. For the purposes of this disclosure, that is one way the OAuth token can be supplied to the digital assistant 310.

At stage 430, the user can perform SSO to log into the EMM system. This can be done prior to or after the linking of stages 410 through 425. The remote application can load on the user device and contact the portal application as part of the SSO. This can establish a session between the portal application and the remote application 320.

At stage 440, bit values can be provided to the portal application (e.g., backend server 330) to define which applications are available to the user's digital assistant 310. In one example, the user can select which applications are available at the remote application 320. The user can select a subset of applications that are available to the user through the portal application. The applications available to the use through the portal application can be based on a profile stored at the management server or backend server 330. In another example, the profile can also dictate which of the applications are available for requests from the digital assistant 310. This can allow an administrator of the EMM system to restrict some applications from being used by the digital assistant 310.

At stage 440, the identity service can provide tokens or other credentials to the portal application. These be credentials can allow access to applications available through the portal application. For example, as part of SSO, a background service can log into the various applications associated with the user's profile. Each application can return an OAuth token or other credential for future communications without further login (while the token or session is active). The credentials can be stored at the identity server 335 or backend server 330 for use by the portal application.

At stage 445, the portal application can receive a request from the linked digital assistant 310. The portal application can match user information from the OAuth token (from the digital assistant 310) to user information from the remote application 320 session. For example, the remote application 320 session can be established with a SAML assertion that contains user information. The user information can be any information used to uniquely identify a user. Example user information can include domain information, an email address, or a user identifier for looking up a user's identity in the EMM system. The portal application can establish the link between an active session and the user associated with the digital assistant 310 either before or after receiving the request. If no session exists, then the portal application can return a message to the digital assistant 310 to prompt the user to establish a session before any requests can be fulfilled.

At stage 450, the portal application can notify the remote application 320 of the request. The notification can display on the user device. For example, a prompt can notify the user that the digital assistant 310 is attempting to access the portal application, and provide the user with buttons to allow or deny. If the user allows the activity, then an authentication session is established. The session can be timed. While active, the authentication session can permit the portal application to handle requests from the digital assistant 310 without further permission from the remote application.

At stage 455, the portal application or digital assistant 310 can send the request to the third-party application 340. In one example, the portal application determines an API call based on the intent or slots received as part of the request from the digital assistant 310. The portal application can then make the API call to the correct service, such as third-party application 340. The API call can be accompanied with a credential collected at stage 440.

Alternatively, the portal application can return an address and a credential to the digital assistant 310. This can allow the digital assistant 310 to communicate with the third-party application 340.

At stage 460, the third-party application 340 can fulfill the request. This can include performing a query or action and returning a result, which can include enterprise data. If the third-party application 340 is an email application, the result can include portions of one or more emails. The third-party application 340 could alternatively be a cloud storage provider, and the result could be retrieving a file that matches a description provided by a user.

In one example, the result is displayed in the remote application 320. Because the remote application 320 is linked to the digital assistant 310, the backend server can provide information to both the digital assistant 310 and the user device. For example, if the result includes a file, a link to the file can be presented at the remote application 320. This can allow the user to simply speak to the digital assistant 310 to easily retrieve a file or email, but do work on the file or email at the user device.

FIGS. 5A-5D include example GUI screens displayed on a user device. When a user attempts to link the digital assistant 310 to the portal application, they can be presented with a login screen 510 of FIG. 5A. The login screen 510 can allow the user to enter a user name and password 516, in an example. The user can also select a domain 514 when multiple domains exist for the tenant at the portal application. Then the user can select an option 512 to sign in.

Figure 5A:
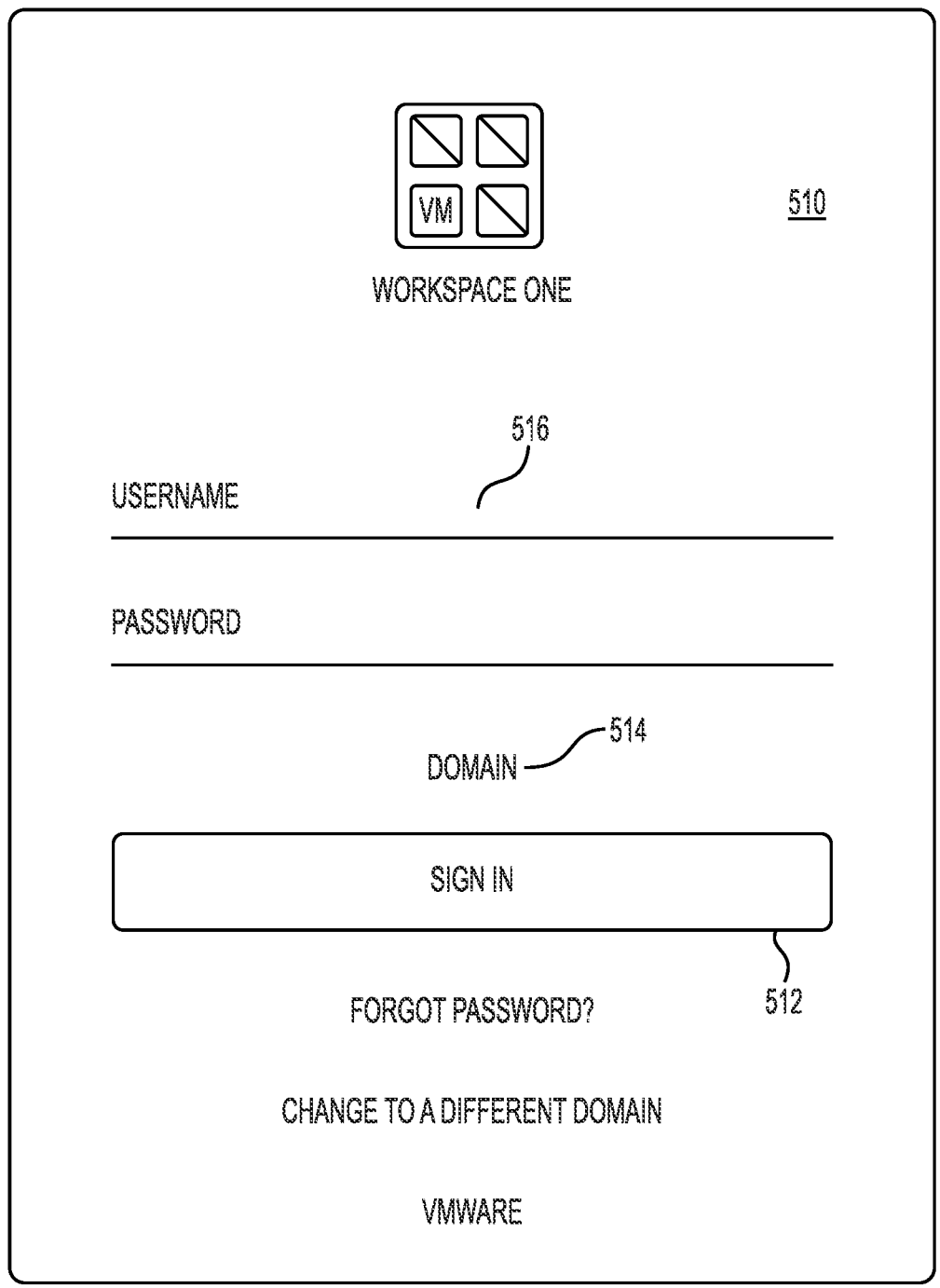
FIG. 5A is an exemplary illustration of a graphical user interface.
Figure 5B:
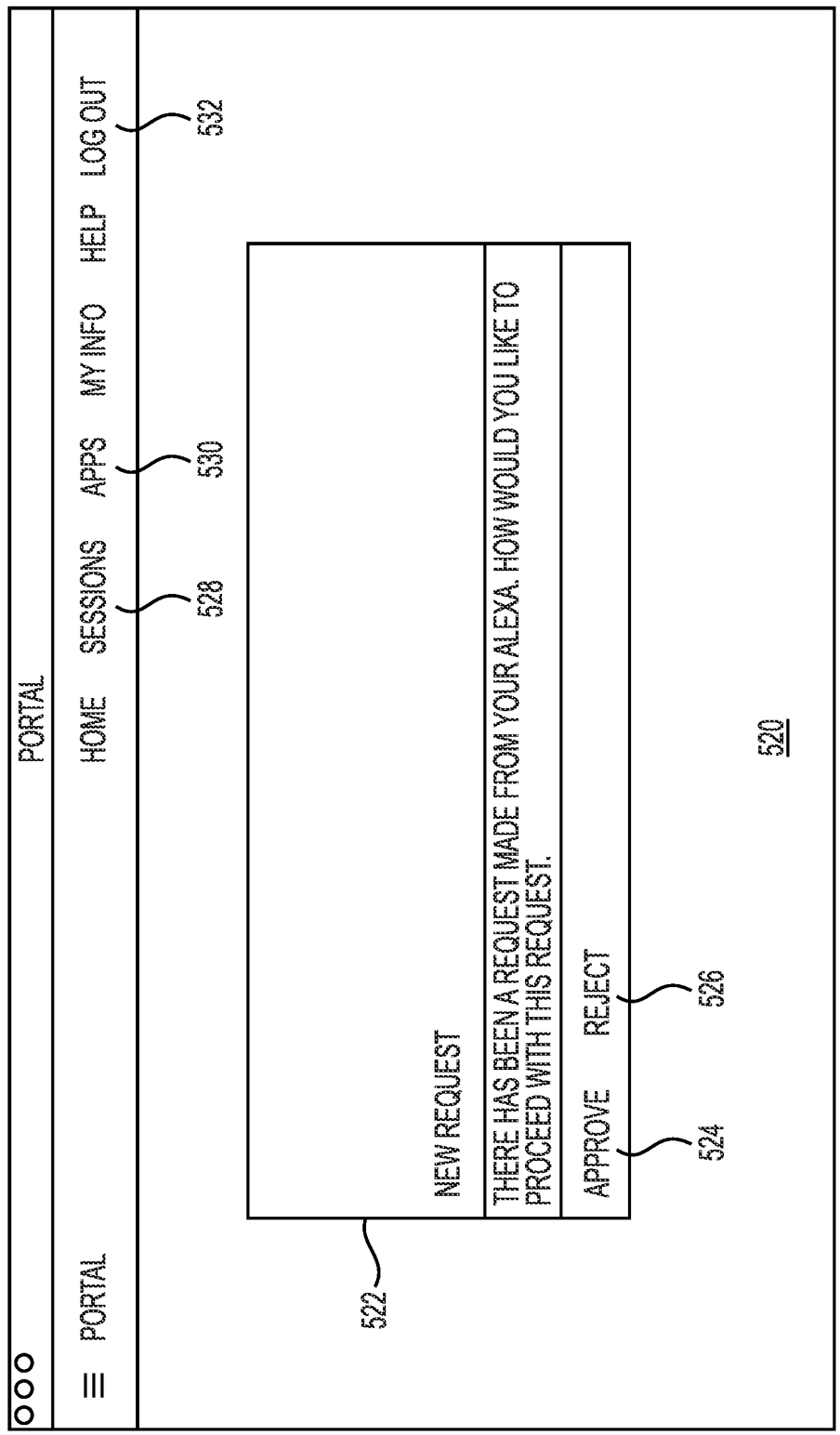
FIG. 5B is an exemplary illustration of a graphical user interface.

After the user has connected to the EMM system, they can be notified at the user device of a request by the digital assistant 310 to access the portal application. FIG. 5B shows an example notification screen 520 that can be displayed on the user device. The notification can include a message 522 that alerts the user that a digital assistant 310 has made a request to the portal application. If the user caused the digital assistant 310 to make the request, then they can approve the request by selecting the approve option 524. Otherwise, they can select a reject option 526 to reject the request.

If the request is approved, the remote application 320 can establish an authorization session with the backend server 330. The digital assistant 310 can make requests without further authorization from the remote application 320 while that session is active.

The remote application 320 can present additional options for managing digital assistant 310 sessions. In one example, the user can select a sessions option 528 to view active sessions. This can also allow a user to select and terminate a session, in an example.

The user can further select an application option 530 for selecting which applications the digital assistant 310 can access through the portal application. In one example, the GUI can list all of the applications available to the user through the portal application. The user can then select which applications the digital assistant 310 can or cannot access. When the selections are saved, an array of bits can be updated at the backend server 330 to control which of the applications the digital assistant 310 can access. If the digital assistant 310 makes a request that needs to be handled by an inaccessible third-party application 340, the portal application can prompt the user at the remote application 320 to enable that access to the third-party application 340.

The remote application 320 can also include an option to log out 532. This can allow the user to end the session between the remote application 320 and the backend server 330.

Figure 5C:
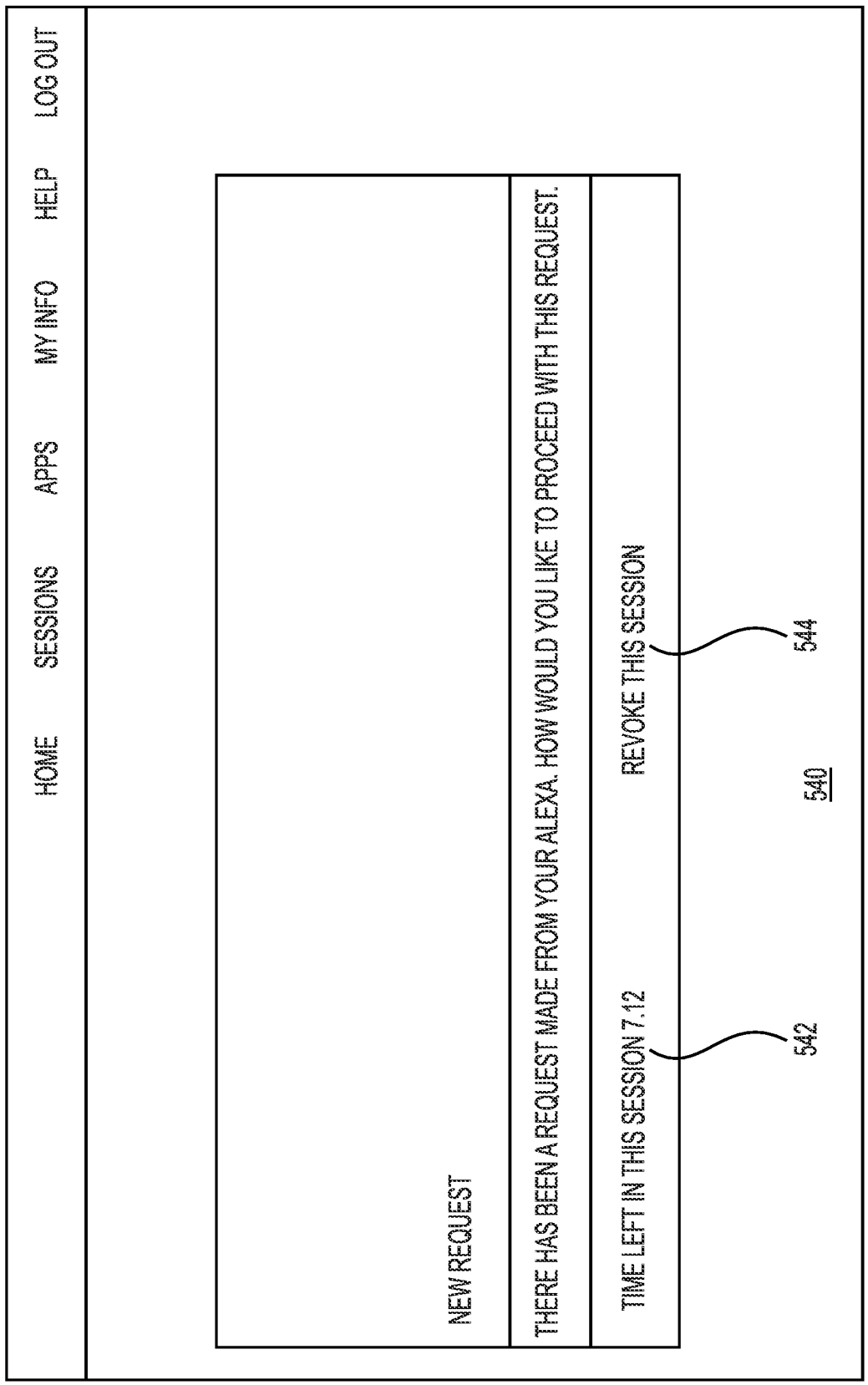
FIG. 5C is an exemplary illustration of a graphical user interface.

Turning to FIG. 5C, when the authorization session begins, the remote application 320 can display a screen 540. This screen can indicate the time left 542 in the authorized session. During this time, the digital assistant 310 can continue to make requests to the portal application. However, the user can also end the session early by choosing an option 544 to revoke the session. This option 544 can cause the backend server 330 to again notify the remote application 320 of any additional request by the digital assistant 310, again requiring user confirmation before fulfilling the request.

Figure 5D:
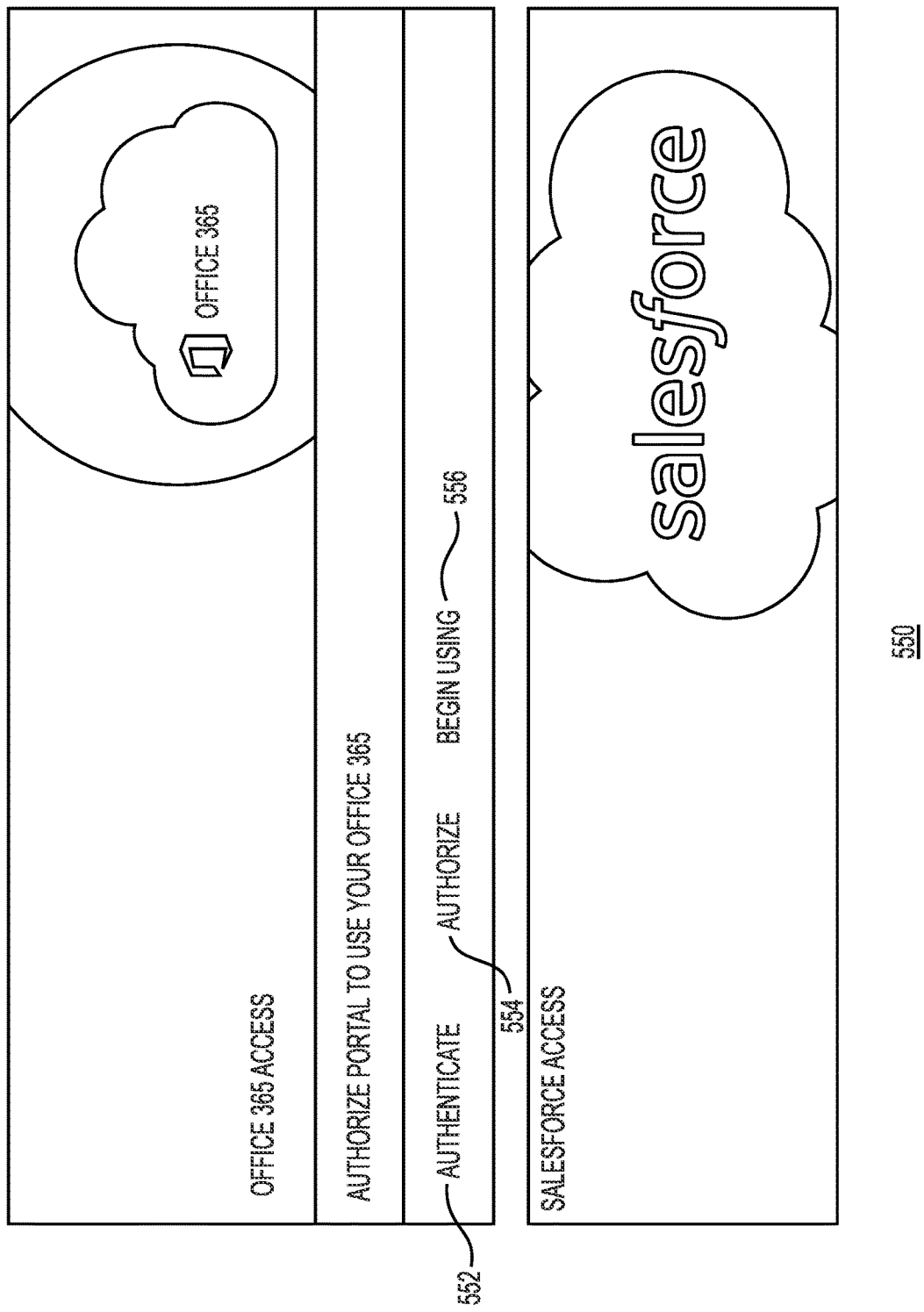
FIG. 5D is an exemplary illustration of a graphical user interface.

FIG. 5D shows an example screen 550 for enabling particular applications for use with the digital assistant 310. In one example, the portal application does not log into every possible application on the user's behalf until the user instructs the portal application to do so. Therefore, in an application screen, such as a screen presented based on application option 530, the user can scroll through and authorize particular applications available through the portal application. In this example, the user can select an option 552 to authenticate with third-party application 340 OFFICE 365. This can cause the backend server 330 or identity service to log into OFFICE 365 based on credentials stored by the identity service.

In one example, a separate option 554 can allow the user to authorize the digital assistant 310 to access the third-party application 340. Prior to authorization, the backend server 330 can block access from the digital assistant 310 to the third-party application 340 even if an authorization session exists. This option can be combined with the authentication option 552 in another example.

Another option 556 can allow the user to use the third-party application 356 from their user device. In one example, actions performed based on requests from the digital assistant 310 can update in real time the GUI being displayed on the user device. As an example, if a user says, "CORTANA, open the portal and delete the most recent email from Mark," the email interface on the user device can update to show the email being deleted.

FIG. 6 is an illustration of example components of a system 600. The digital assistant 310 can be a computing device having a processor that receives and interprets audio commands. It can be a stand-alone device separate from the user device 620. It can alternatively also be a phone, tablet, laptop, or other processor-based device that executes software for listening and performing tasks.

When the digital assistant 310 receives an audio request, it can parse the audio into intents and slots 610. This can be done at the digital assistant 310 or at a server that the digital assistant 310 contacts. The intent can dictate which service the digital assistant contacts to fulfill the request. In this example, the intent can indicate that the backend server 330 of the portal application 630 should be contacted.

The backend server 330 can be one or more servers that execute portions of the portal application 630. The backend server 330 can also store bits 634 to indicate which applications 650 are accessible by the digital assistant 310 when a session is active.

In this example, the digital assistant 310 can send an intent and slots 610 to the backend server 330 as part of a request. The request can be accompanied with an OAuth token received as part of linking the digital assistant 310 to the portal application 630. The OAuth token can identify the user. The OAuth token can be generated by the identity server 335, in an example. The identity server 335 can be part of the backend server 330 or can be one or more separate servers. The identity server 335 can handle user authentication, in one example.

The user device 620 can be any processor-based device, such as a phone, laptop, tablet, or personal computer. The user device 620 can enroll in the EMM system at the backend server 330 or a separate management server (not pictured). Enrollment can allow the EMM system to configure a profile for the user. The profile can dictate which applications 650 are available to the user through the portal application 630.

In one example, the remote application 320 is installed on the user device 620 as part of enrollment. The remote application 320 can be part of a management agent that allows the backend server 330 or management server to control enterprise-related functionality on the user device 620. Alternatively, the remote application 320 can be a web application that the user accesses with an internet browser. In one example, during enrollment, the user can receive a login or other credentials needed to access the portal application 630.

The remote application 320 can authenticate the user device 620 with the EMM system by authenticating with the identity server 335, in an example. This authentication can be part of SSO. When the user authenticates, the identity server 335 can direct the remote application 320 to connect to the backend server 330, in an example. This can cause the user device 620 to make a SAML assertion that identifies the user to the backend server 330 and starts a session with the backend server 330.

When the SAML assertion and OAuth token both identify the same user, the backend server 330 can link the digital assistant 310 to the remote application 320 of the user device 620. This can allow the backend server 330 to verify with the user at the user device 620 before authorizing a session for the digital assistant 310 at the portal application 630.

The identity server 335 can maintain a credential library 635 for logging the user into the applications 650, including third-party application 340. This can be used as part of SSO. Once the identity server 335 has authenticated the user, the identity server can supply the appropriate stored credentials, such as user names, passwords, or tokens, to log into the various third-party applications 340, 650. This can also prevent the digital assistant 310 from having to individually log into each application 650 in an example.

In one example, the third-party application 340 can be an email application that accesses enterprise email 640. The email 640 can be returned to the backend server 330, which in turn can send some or all of the email 640 to the digital assistant 310 for reading to the user. In one example, only the necessary text, such as the subject and body, of the email 640 is returned to the digital assistant 310. Based on voice requests at the digital assistant 310, the backend server 330 can also return results to the remote application 320. This can allow the remote application 320 to visually display results as they are being described by the digital assistant 310.

In one example, the backend server 330 can cause the remote application 320 to perform functions based on the digital assistant 310 request. For example, the remote application can open the third-party application 340 and display email 640 that was requested by the digital assistant 310, in an example. The backend server 330 can communicate with the user device 620 through push notifications and instructions to the remote application 320 based on the active session.

In an alternate example, the digital assistant 310 can be part of the remote application 320. In that example, the remote application 320 can handle the voice functions of the digital assistant 310 while also allowing the user to validate the remote application 320 session with the portal application.

Other components of FIG. 6 can also be combined in other examples. In addition to building the digital assistant 310 into the remote application 320, the identity server 335 can be built into the backend server 330. Similarly, the intent and slots 610 functionality can be built into the backend server 330 in an example. This can allow the backend server 330 to directly determine appropriate API calls. The API calls can be specific to the applications 650 implicated by a request. By bypassing a separate digital assistant 310 server, the security of the process can increase, in an example.

Other examples of the disclosure will be apparent to those skilled in the art from consideration of the specification and practice of the examples disclosed herein. The examples are not limited to an enterprise environment, and may be applied at educational facilities or other environments. The third party app need not be a third party app. For example, a company could put the whole system together within their own ecosystem.

Though some of the described methods have been presented as a series of steps, it should be appreciated that one or more steps can occur simultaneously, in an overlapping fashion, or in a different order. The order of steps presented is only illustrative of the possibilities and those steps can be executed or performed in any suitable fashion. Moreover, the various features of the examples described here are not mutually exclusive. Rather any feature of any example described here can be incorporated into any other suitable example. It is intended that the specification and examples be considered as exemplary only, with a true scope and spirit of the disclosure being indicated by the following claims.

What is claimed is:

1. A method for accessing a secured application within an enterprise mobility management ("EMM") system using a digital assistant, comprising:
   receiving, at a secured backend server within an EMM system, a request to access a secured application from a digital assistant outside the EMM system;
   determining, by the secured backend server, that first user information received from the digital assistant matches second user information received from a remote application installed on a user device previously enrolled in the EMM system;
   sending, from the secured backend server, a notification of the request to the remote application installed on the user device; and
   in response to the notification, receiving a confirmation at the secured backend server granting the digital assistant access to the secured application from the remote application installed on the user device.

2. The method of claim 1, further comprising establishing a session between the remote application and a portal application of the EMM system as part of a single sign on ("SSO") that identifies the user.

3. The method of claim 2, further comprising authenticating the session by sending a Security Assertion Markup Language ("SAML") assertion that identifies the user to the portal application.

4. The method of claim 1, wherein establishing the session automatically causes the portal application to retrieve an access credential for the secured application, wherein the secured application is a third-party application.

5. The method of claim 1, further comprising:
   receiving a request at the secured backend server, from the remote application installed at the user device, to end the session; and
   notifying the portal application to deny the digital assistant access to the secured application.

6. The method of claim 1, further comprising:
   establishing a session between the remote application and a portal application of the EMM system,
   wherein establishing the session includes authenticating with an identity server that stores credentials for a plurality of applications, wherein the plurality of applications includes the secured application.

7. The method of claim 6, further comprising allowing the digital assistant to send requests to the plurality of applications without further input from the remote application for a defined period of time.

8. A non-transitory, computer-readable medium containing instructions executed by at least one processor to perform stages for accessing a secured application within an enterprise mobility management ("EMM") system using a digital assistant, the stages comprising:
   receiving, at a secured backend server within an EMM system, a request to access a secured application from a digital assistant outside the EMM system;
   determining, by the secured backend server, that first user information received from the digital assistant matches second user information received from a remote application installed on a user device previously enrolled in the EMM system;
   sending, from the secured backend server, a notification of the request to the remote application installed on the user device; and
   in response to the notification, receiving a confirmation at the secured backend server granting the digital assistant access to the secured application from the remote application installed on the user device.

9. The non-transitory, computer-readable medium of claim 8, the stages further comprising establishing a session between the remote application and a portal application of the EMM system as part of a single sign on ("SSO") that identifies the user.

10. The non-transitory, computer-readable medium of claim 9, the stages further comprising authenticating the session by sending a Security Assertion Markup Language ("SAML") assertion that identifies the user to the portal application.

11. The non-transitory, computer-readable medium of claim 8, wherein establishing the session automatically causes the portal application to retrieve an access credential for the secured application, wherein the secured application is a third-party application.

12. The non-transitory, computer-readable medium of claim 8, the stages further comprising:
    receiving a request at the secured backend server, from the remote application installed at the user device, to end the session; and
    notifying the portal application to deny the digital assistant access to the secured application.

13. The non-transitory, computer-readable medium of claim 8, the stages further comprising:
    establishing a session between the remote application and a portal application of the EMM system,
    wherein establishing the session includes authenticating with an identity server that stores credentials for a plurality of applications, wherein the plurality of applications includes the secured application.

14. The non-transitory, computer-readable medium of claim 13, the stages further comprising allowing the digital assistant to send requests to the plurality of applications without further input from the remote application for a defined period of time.

15. A system for accessing a secured application within an enterprise mobility management ("EMM") system using a digital assistant, comprising:
    a non-transitory, computer-readable medium containing instructions;
    a processor that executes the instructions to perform stages, comprising:
      receiving, at a secured backend server within an EMM system, a request to access a secured application from a digital assistant outside the EMM system;
      determining, by the secured backend server, that first user information received from the digital assistant matches second user information received from a remote application installed on a user device previously enrolled in the EMM system;
      sending, from the secured backend server, a notification of the request to the remote application installed on the user device; and
      in response to the notification, receiving a confirmation at the secured backend server granting the digital assistant access to the secured application from the remote application installed on the user device.

16. The non-transitory, computer-readable medium of claim 15, the stages further comprising establishing a session between the remote application and a portal application of the EMM system as part of a single sign on ("SSO") that identifies the user.

17. The non-transitory, computer-readable medium of claim 15, wherein establishing the session automatically causes the portal application to retrieve an access credential for the secured application, wherein the secured application is a third-party application.

18. The non-transitory, computer-readable medium of claim 15, the stages further comprising:
   receiving a request at the secured backend server, from the remote application installed at the user device, to end the session; and
   notifying the portal application to deny the digital assistant access to the secured application.

19. The non-transitory, computer-readable medium of claim 15, the stages further comprising:
   establishing a session between the remote application and a portal application of the EMM system,
   wherein establishing the session includes authenticating with an identity server that stores credentials for a plurality of applications, wherein the plurality of applications includes the secured application.

20. The non-transitory, computer-readable medium of claim 19, the stages further comprising allowing the digital assistant to send requests to the plurality of applications without further input from the remote application for a defined period of time.

* * * * *